United States Patent
Rapacki et al.

(10) Patent No.: US 8,210,902 B2
(45) Date of Patent: Jul. 3, 2012

(54) SURFACE TREATED IMPLANTABLE ARTICLES AND RELATED METHODS

(75) Inventors: Alan R. Rapacki, Redwood City, CA (US); Wilhelm Leung, Burnaby (CA)

(73) Assignee: QLT Inc., Vancouver (CA)

( * ) Notice: Subject to any disclaimer, the term of this patent is extended or adjusted under 35 U.S.C. 154(b) by 930 days.

(21) Appl. No.: 12/283,002

(22) Filed: Sep. 5, 2008

(65) Prior Publication Data

US 2009/0298390 A1    Dec. 3, 2009

Related U.S. Application Data

(60) Provisional application No. 61/057,246, filed on May 30, 2008, provisional application No. 61/132,927, filed on Jun. 24, 2008.

(51) Int. Cl.
*B24B 1/00* (2006.01)
(52) U.S. Cl. ............. 451/32; 451/35; 451/36; 451/57
(58) Field of Classification Search .............. 451/32, 451/34, 35, 36, 57, 103, 104, 113, 326, 327, 451/328, 329, 330
See application file for complete search history.

(56) References Cited

U.S. PATENT DOCUMENTS

| | | | | |
|---|---|---|---|---|
| 3,848,363 | A * | 11/1974 | Lovness et al. | 451/36 |
| 5,128,058 | A | 7/1992 | Ishii et al. | |
| 5,133,159 | A * | 7/1992 | Nelson | 451/32 |
| 5,766,243 | A * | 6/1998 | Christensen et al. | 128/898 |
| 5,961,370 | A | 10/1999 | Valle et al. | |
| 5,962,383 | A | 10/1999 | Doyel et al. | |
| 6,010,391 | A | 1/2000 | Lewellen et al. | |
| 6,095,901 | A * | 8/2000 | Robinson et al. | 451/35 |
| 6,729,939 | B2 | 5/2004 | Wrue | |
| 6,866,563 | B2 | 3/2005 | Green | |
| 2007/0048661 | A1 * | 3/2007 | Kawauchi | 430/270.1 |
| 2007/0132125 | A1 | 6/2007 | Rastogi et al. | |
| 2008/0020127 | A1 | 1/2008 | Whiteford et al. | |
| 2008/0113245 | A1 * | 5/2008 | Liu et al. | 429/34 |

FOREIGN PATENT DOCUMENTS

| | | |
|---|---|---|
| EP | 0442745 A1 | 8/1991 |
| JP | 2000204321 | 7/2000 |

OTHER PUBLICATIONS

"International Application Serial No. PCT/US2008/010501, International Search Report mailed Mar. 3, 2009", 4 pgs.
"International Application Serial No. PCT/US2008/010501, Written Opinion mailed Mar. 3, 2009", 9 pgs.

* cited by examiner

*Primary Examiner* — Eileen P. Morgan
(74) *Attorney, Agent, or Firm* — Pillsbury Winthrop Shaw Pittman LLP

(57) ABSTRACT

Surface treated implantable articles and related methods are disclosed. The surface treated implantable articles can be substantially flash-free, include one or more rounded edges, or include an enhanced optical clarity, one or all of which can be produced by polishing. The polishing can include causing the implantable articles to be repeatedly impacted with polishing media when the articles are swelled to an enlarged state. The polishing process can be particularly useful for smoothing lacrimal implants insertable in a lacrimal canaliculus.

17 Claims, 4 Drawing Sheets

SURFACE TREATED IMPLANTABLE ARTICLES AND RELATED METHODS

CLAIM OF PRIORITY

This non-provisional application claims the benefit of priority under 35 U.S.C. §119(e) to U.S. Provisional Patent Application Ser. No. 61/057,246 filed on May 30, 2008 and U.S. Provisional Patent Application Ser. No. 61/132,927 filed on Jun. 24, 2008, the specifications of which are herein incorporated by reference in their entirety.

TECHNICAL FIELD

This patent document pertains generally to ophthalmic articles, and particularly to ocular implantable articles. More particularly, but not by way of limitation, this patent document pertains to ocular implantable articles that are substantially flash-free and include one or more rounded edges produced by a polishing process, such as during article fabrication.

BACKGROUND

Methods exist for molding articles from a moldable material, such as plastic. One problem with molding is that it can form excess flash material, sharp edges, uncured article material regions or other irregularities in a molded article's structure.

EXEMPLARY ASPECTS AND EMBODIMENTS OF THE INVENTION

The present inventors have recognized, among other things, that depending on the type of article molded and the manner in which the article is to be used, the existence of excess flash material, sharp edges, uncured article material regions or other irregularities (e.g., surface irregularities) can be undesirable. Unfortunately, obtaining a highly polished, smooth finished article is often difficult when curing a material in a mold. Even the most precise molding die result in some flashing, sharp edges, uncured article material regions or other irregularities. The resulting articles can be hand-trimmed and hand-polished, but this can be time consuming, expensive or imprecise and may not result in the regular, uniform surface desired. Further, many molded articles, particularly those for medical applications, are relatively small or irregularly shaped, thereby causing difficulties in manually obtaining the desired smooth finish.

The present inventors have also recognized, among other things, a promising approach to polishing a molded silicone or other soft durometer (e.g., polyurethane) implantable article can include increasing the article's size, such as by using a swellable solvent, and then continuously (e.g., on a recurring or ongoing basis) impacting the enlarged article, such as with various sizes of polishing media for a period of time. It has been found that a polishing process using a swellable solvent can also change a stiffness of the implantable article by removing any uncured silicone, for example, from a molded article. In brief, the present inventors have found that a polishing process can be designed to remove excess flash material, sharp edges, uncured article material regions or other surface irregularities from an article. This polishing process can also be designed to enhance the article's optical clarity.

Improving the surface finish of an implantable article can, in turn, call for less insertion force to implant the article, reduce the potential for damage to an inner cellular layer of tissue into which the article is received, or inhibit attachment of micro-organisms to the surface of the article. For instance, it has been found that sharp edges and surface irregularities can prevent the flow of bodily fluids around an implanted article, thereby creating stagnant or near stagnant reservoirs encouraging microbial growth. By improving an article's surface finish, the movement of bodily fluids can be enhanced and provide a natural defense mechanism to article surface microbial growth.

This patent document describes surface treated implantable articles and related methods. The surface treated implantable articles can be substantially flash-free, include one or more rounded edges, or include an enhanced optical clarity, one or all of which can be produced by a present polishing process. This can be desirable in medical applications. For instance, surface treated implantable articles such as lacrimal implants insertable into a lacrimal canaliculus can be placed in direct contact with ocular bodily tissues without rupturing one or more blood vessels, or irritating or causing other tissue trauma. The polishing process can include causing the implantable articles to be continuously (e.g., on a recurring or ongoing basis) impacted with polishing media while in an enlarged, swelled state. This can smooth one or more surfaces or edges of the implantable articles.

To better illustrate the subject matter described herein, a non-limiting list of exemplary aspects and embodiments is provided here:

1. A method comprising:
   placing one or more implantable articles in a receptacle containing a polishing mixture, the polishing mixture comprising a solvent and a polishing media including particles having two or more different sizes, at least one of the particle sizes greater than about 3 millimeters across;
   causing the implantable articles to be repeatedly impacted with the polishing mixture so as to smooth one or both of a surface or an edge of the implantable articles; and
   separating the implantable articles from the polishing mixture, thereby producing one or more polished implantable articles.
2. The method according to aspect 1, comprising swelling the implantable articles using the solvent, and causing the implantable articles to be repeatedly impacted with the polishing media while in a swelled state.
3. The method according to any of aspects 1 or 2, comprising swelling the implantable articles using at least one of xylenes, naphthalene, toluene, or methylene chloride.
4. The method according to any of aspects 1-3, wherein repeatedly impacting the implantable articles includes tumbling the implantable articles and the polishing mixture together for a period of time and at a speed sufficient to smooth one or both of a surface or an edge of the implantable articles.
5. The method according to any of aspects 1-4, wherein repeatedly impacting the implantable articles includes at least one of removing article flash, removing uncured article material, rounding an article edge, or improving article optical clarity.
6. The method according to any of aspects 1-5, wherein separating the implantable articles includes removing residual solvent from the implantable articles.
7. The method according to aspect 6, comprising detecting a residual solvent amount of the one or more polished implantable articles.
8. The method according to aspect 7, wherein detecting the residual solvent amount includes using a headspace gas chromatographic method using a flame ionization detector and a headspace autosampler to detect a residual of methylene chloride of about 0.1125 micrograms or greater.

9. The method according to any of aspects 1-8, comprising providing the polishing media, wherein the polishing media include particle sizes of about 1 millimeter across, about 3 millimeters across, and about 6 millimeters across in about a 2:1:1 ratio.

10. The method according to any of aspects 1-9, comprising providing the implantable articles, wherein the implantable articles include one or more lacrimal implants insertable into a lacrimal canaliculus.

11. The method according to aspect 10, wherein at least one of the lacrimal implants comprise an implant body, including first and second portions, and extending from a proximal end of the first portion to a distal end of the second portion; the first portion defining a longitudinal proximal axis and the distal end defining a longitudinal distal axis; the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature.

12. The method according to any of aspects 1-11, comprising providing the implantable articles, wherein the implantable articles include a silicone or polyurethane material.

13. The method according to any of aspects 1-12, comprising cleaning the implantable articles, including contacting the implantable articles with a cleaning solution in a receptacle and agitating the receptacle for a period of time and at a speed sufficient to clean a surface of the implantable articles.

14. A method comprising:
    introducing into a receptacle contents comprising one or more implantable silicone articles and a polishing mixture, the polishing mixture including polishing media and a swelling-promoting solvent; and
    agitating the contents of the receptacle for a time sufficient to remove one or more surface irregularities from the implantable silicone articles.

15. The method according to aspect 14, wherein agitating includes abrading a surface of the implantable silicone articles by repeatedly impacting the implantable silicone articles, while in a swelled state, with the polishing media.

16. The method according to any of aspects 14 or 15, wherein agitating includes burnishing a surface of the implantable silicone articles by repeatedly impacting the implantable silicone articles, while in a swelled state, with the polishing media.

17. The method according to any of aspects 14-16, wherein agitating includes rotating the receptacle at a speed and for a time sufficient to substantially remove the one or more surface irregularities from the implantable silicone articles.

18. The method according to any of aspects 14-17, comprising providing the polishing media, wherein the polishing media include particles exceeding 3 millimeters across.

19. The method according to any of aspects 14-18, comprising removing residual solvent from the implantable silicone articles, including heating the implantable silicone articles to at least about 100° F.

20. The method according to any of aspects 14-19, comprising detecting one or more polished implantable articles substantially free of residual solvent using a flame ionization detector.

21. A polished implantable article comprising:
    an article body having at least one outer surface and at least one edge, the at least one outer surface substantially free of article flash and uncured article material and the at least one edge having a rounded configuration; and wherein the article body has previously been enlarged using a swelling-promoting solvent and subjected to repeated impacting, while in an enlarged state, with a polishing media including particles having two or more different sizes, at least one of the particle sizes greater than about 3 millimeters across.

22. The polished implantable article according to aspect 21, wherein the article body has previously been enlarged using methylene chloride.

23. The polished implantable article according to any of aspects 21 or 22, wherein the article body includes silicone.

24. The polished implantable article according to any of aspects 21-23, wherein the article body includes a lacrimal implant body, including first and second portions, the lacrimal implant body configured such that, when implanted in a lacrimal canaliculus, an outer surface of at least the second portion is biased against at least a portion of the lacrimal canaliculus.

25. The polished implantable article according to any of aspects 21-24, wherein the at least one outer surface and the at least one edge is substantially free of the swelling-promoting solvent.

These and other embodiments, advantages, and aspects of the present surface treated implantable articles and methods are set forth, in part, in the following Detailed Description. This Summary is intended to provide an overview of the subject matter of the present patent document. It is not intended to provide an exclusive or exhaustive explanation of the present subject matter. The Detailed Description is included to provide further information about the subject matter of the present patent document.

BRIEF DESCRIPTION OF THE DRAWINGS

In the drawings, like numerals have been used to describe similar components throughout the several views. Like numerals having different letter suffixes have been used to represent different instances of similar components. The drawings illustrate generally, by way of example, but not by way of limitation, various embodiments discussed in the present document.

DETAILED DESCRIPTION

This patent document describes surface treated implantable articles and related methods. The surface treated implantable articles can be substantially flash-free, can include one or more rounded edges, or can include an enhanced optical clarity, for example, one or all of which can be produced by a present polishing process. The polishing process can include causing the implantable articles to be impacted with polishing media during an ongoing period of time in which the articles are in an enlarged, swelled state. This can smooth one or more surfaces or edges of the implantable articles. In various examples, the polishing media can include at least some granules that are greater than about 3 millimeters in diameter.

Figure 1:
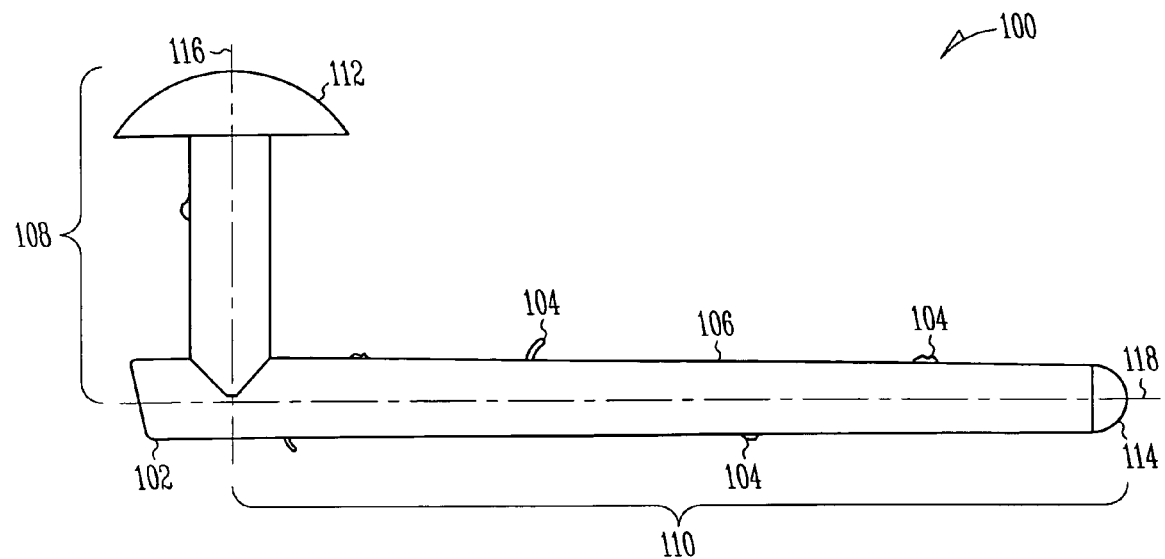
FIG. 1 illustrates an example of a side view of an implantable article prior to undergoing a present polishing process.

FIG. 1 illustrates an example of a side view of an implantable article 100 before undergoing a present polishing process. As a result of a molding or other fabrication process, sharp edges 102, excess material ("flash") 104, uncured article material regions or other irregularities may be formed about a peripheral surface of the implantable article 100, as shown. These sharp edges 102, flash 104, uncured article material regions or other irregularities can cause the implantable article 100 to snag on bodily tissue, such as when the article 100 is being implanted. This can result in pain or discomfort to a patient.

In some examples, such as is shown FIG. 1, the implantable article 100 includes a lacrimal implant molded for insertion through a lacrimal canaliculus adjacent an eye. The lacrimal implant can comprise an implant body 106 including first 108 and second 110 portions, and can extend from a proximal end 112 of the first portion 108 to a distal end 114 of the second portion 110. The proximal end 112 can define a longitudinal proximal axis 116 and the distal end 114 can define a longitudinal distal axis 118. The implant body 106 can be configured such that, when implanted in the lacrimal canaliculus, an angled intersection (e.g., an at least 45 degree angled intersection) exists between the proximal axis 116 and the distal axis 118 for biasing at least a portion of the implant body 106 against at least a portion of the canaliculus located at or more distal to a canaliculus curvature (i.e., the region at which a lacrimal canaliculus turns from a vertical orientation to a more horizontal orientation).

Further discussion regarding lacrimal implants insertable into a lacrimal canaliculus can be found in commonly-owned Jain et al., U.S. Patent Application No. 61/049,347 filed on Apr. 30, 2008, entitled "LACRIMAL IMPLANTS AND RELATED METHODS," commonly-owned Rapacki et al., U.S. patent application Ser. No. 12/231,989 filed on Sep. 8, 2008, titled "LACRIMAL IMPLANTS AND RELATED METHODS," commonly-owned Sim et al., U.S. Patent Application No. 61/049,337 filed on Apr. 30, 2008, entitled "LACRIMAL IMPLANTS AND RELATED METHODS," commonly-owned Sim et al., U.S. Patent Application No. 61/049,329 filed on Apr. 30, 2008, titled "COMPOSITE LACRIMAL INSERT," and commonly-owned Jain Utkhede et al., U.S. patent application Ser. No. 12/231,986 filed on Sep. 5, 2008, entitled "DRUG CORES FOR SUSTAINED RELEASE OF THERAPEUTIC AGENTS," all of which are herein incorporated by reference in their entirety. In lacrimal implant examples, unpolished sharp article edges 102 or article flash 104 may snag the tissues of a lacrimal punctum and associated canaliculus when implanting the article 100, resulting in discomfort to the patient. Beyond lacrimal implants, the implantable article 100 can include a canalicular stent, an intraocular lens, or other medical implant, for example.

The implantable article 100 can be formed by injecting a silicone or other soft durometer material (e.g., polyurethane) in a mold, curing or hardening the material within the mold, and removing the cured or hardened article 100 from the mold. The molding process can be accomplished using conventional impact molding processes or compression, injection, extrusion or transfer molding. Alternatively, the implantable article 100 can be manufactured using other suitable manufacturing techniques, such as machining or casting. Silicone materials including silicone rubbers and silicone elastomers, are materials that are generally compatible with biological tissues and fluids and provide one suitable option for the formation of the implantable article 100. Other desirable characteristics of silicone materials include their flexibility, ease of molding, and relatively low cost. Suitable polyurethanes for the implantable article 100 can include, but are not limited to, one or a combination of polyurethane elastomers prepared from hydroxyl-terminated polyesters, hydroxy-terminated polyethers, aliphatic, alicyclic or aromatic diisocyanates, or glycol chain extenders.

Certain of the present polishing techniques can use a tumbling or other agitation (e.g., stirring, shaking, multiple directional mixing, or vibrating) process, which can be designed to be compatible with relatively soft implantable articles, such as silicone or polyurethane articles, and be relatively efficient and cost effective. These processes can be employed to remove excess flash 104, sharp edges 102, uncured article material regions or other irregularities resulting from the molding or other manufacture forming process.

Figure 2:
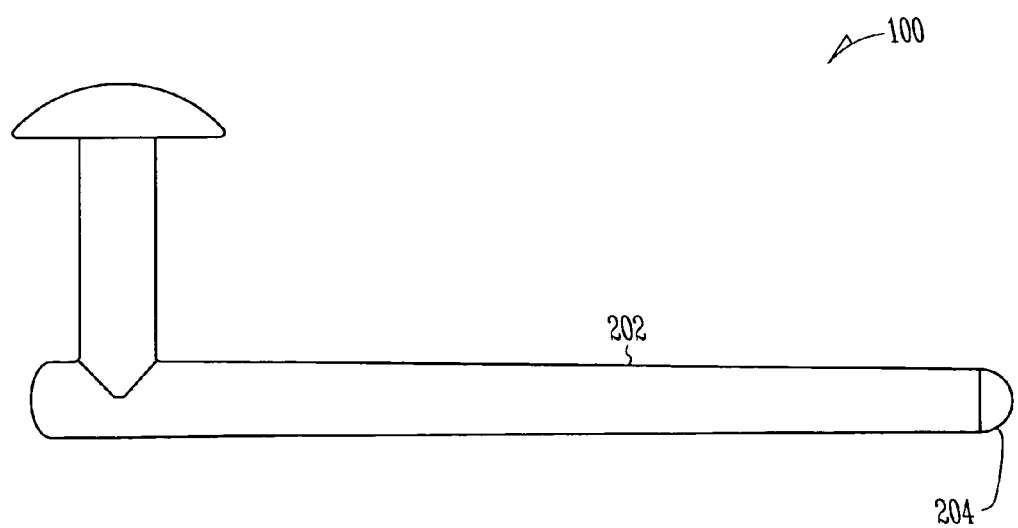
FIG. 2 illustrates an example of a side view of an implantable article after undergoing a present polishing process.

FIG. 2 illustrates an example of a side view of an implantable article 100 after undergoing a present polishing process. As a result, one or more surfaces 202 of the implantable article 100 are substantially flash-free, one or more edges 204 are rounded, one or more uncured article material regions are removed, or an optical clarity of the article is enhanced.

In some examples, one or more implantable articles 100 can be placed in a receptacle along with a polishing mixture. The polishing mixture can include a solvent and polishing media. The contents of the receptacle can then be agitated (e.g., tumbled, stirred, shaken, mixed, vibrated, or the like), such as at a speed and for a duration that permits the articles 100 to attain a desired finish. The precise combination of factors used (e.g., the particular solvent, the type and size of the polishing media, the size of the receptacle, the number of implantable articles 100 agitated, or the speed or time of agitation) can vary, such as with the size, shape, or other characteristics (e.g., article material) of the articles 100 to be polished or the desired degree of polishing.

The polishing process can be performed in a variety of receptacles. The receptacles can be of various sizes or shapes. The receptacles can be formed of glass, polypropylene, polyethylene, stainless steel, or other suitable material. In various examples, the polishing can be performed in a closed receptacle, such as when the solvent used exhibits volatility or toxicity. The closed receptacle can also inhibit the solvent from evaporating into the atmosphere before polishing is complete. The receptacle can be agitated so as to provide enough polishing action of the contained implantable articles 100.

Figure 3:
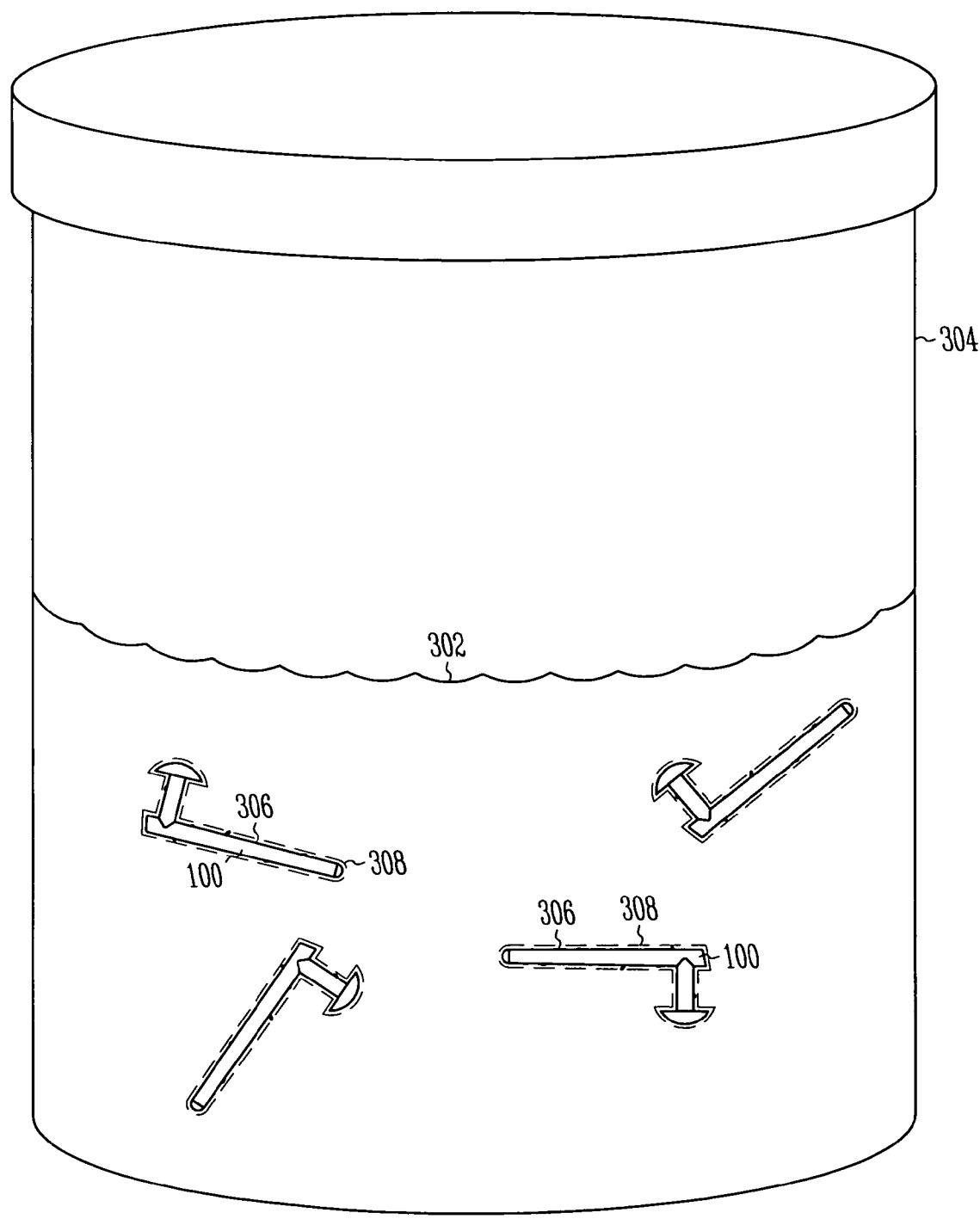
FIG. 3 illustrates an example of a schematic view of a plurality of implantable articles immersed in a swellable solvent within a closed receptacle.

FIG. 3 illustrates an example of a schematic view of a plurality of implantable articles 100 immersed in a swellable solvent 302 within a closed receptacle 304. The number of implantable articles 100 to be polished during a given process can vary, but in various examples, can include about 1 to about 500 articles 100.

In some examples, the solvent 302 can be configured or selected to swell a silicone or other soft durometer implantable article 100 from an original first size 306 to a second size 308 that exceeds the first size 306. In various examples, the solvent 302 used is one or both of USP or NF grade. In certain examples, such swelling can be produced by a chemical agent with a relatively high kauri-butanol (k.b.) value. Examples of such agents can include, but are not limited to, xylenes, naphthalene, toluene, and methylene chloride. Methylene chloride, for example, can be purchased in high qualities with low levels of impurities. Some available solvent compounds can also be used to achieve this swelling of the articles 100. The swelling of the article 100 is thought to improve the polishing ability of a polishing media by increasing the contactable article surface area. Each implantable article 100 can expand substantially isotropically approximately 30% after being soaked in methylene chloride for about 2 minutes. In some examples, a suitable amount of solvent 302 for a given polishing process can be that which covers the standing volume of the polishing media (see, e.g., FIG. 4).

Figure 4:
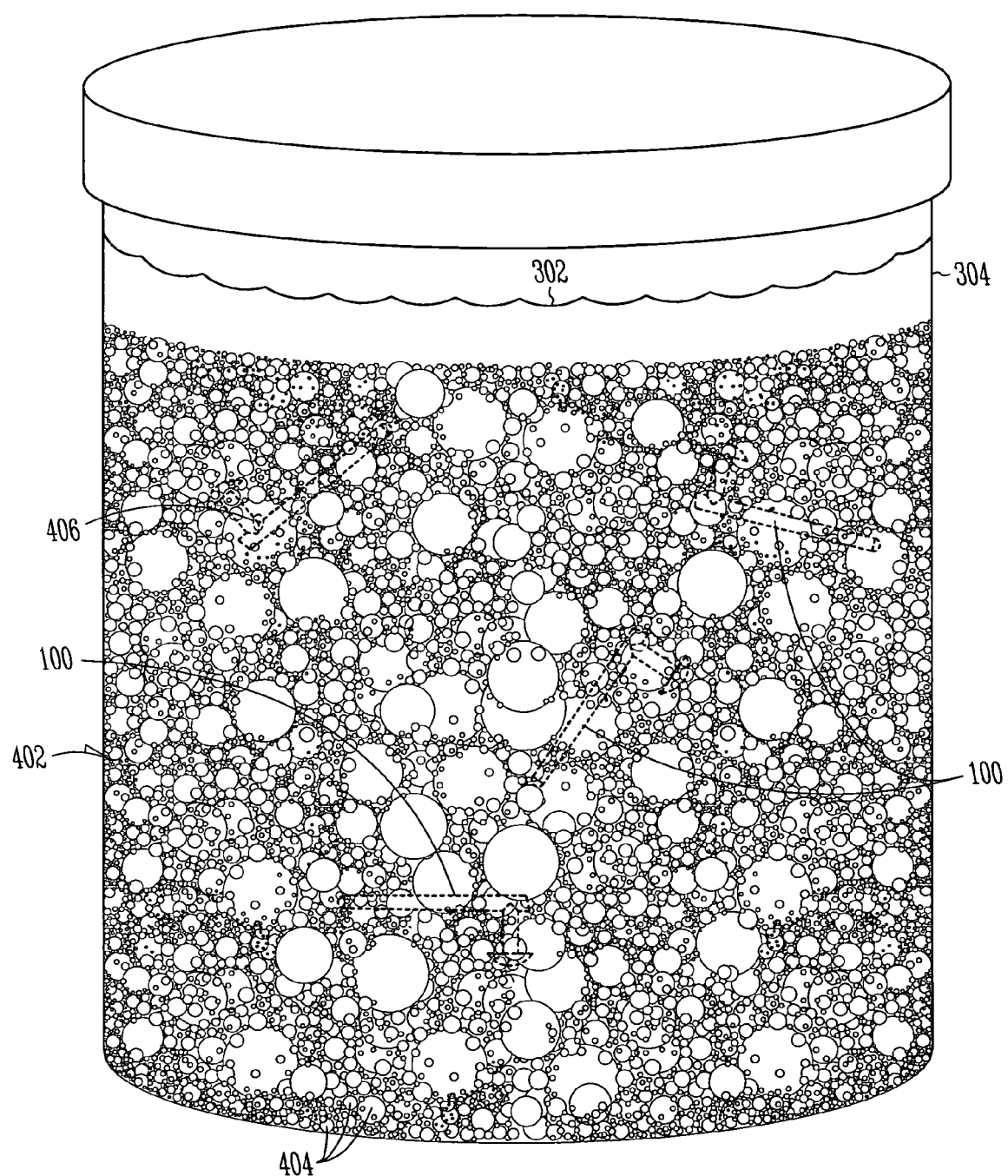
FIG. 4 illustrates an example of a schematic view of a plurality of implantable articles immersed in a polishing mixture, including a swellable solvent and polishing media, within a closed receptacle.

FIG. 4 illustrates an example of a schematic view of a plurality of implantable articles 100 immersed in a polishing mixture 402 (e.g., including a swellable solvent 302 and polishing media 404) within a closed receptacle 304. During polishing, the polishing media 404 repeatedly impact the implantable articles 100. This can smooth one or more surfaces or edges of the articles 100. The polishing media 404 can include a wide variety of materials, shapes, or sizes, or can include a combination of several different materials. Examples of polishing media 404 material can include, but are not limited to, ceramic, porcelain, plastic, organic or stainless steel. The polishing media 404 can, for example, range from small somewhat round sand-like particles or granules to larger sizes or triangular, cylindrical, or other shapes. In some examples, the polishing media 404 can include substantially spherical balls. For more aggressive polishing, an abrasive powder such as alumina or silica, can be added to the mixture 402 or adhered to an outer surface of particles in the polishing media 404 to wear down the articles 100 by scraping or rubbing. In various examples, the polishing media 404 is selected so as to not impart or embed particles into the implantable articles 100.

The choice of polishing media 404 particle sizes can be important as different sized media 404 can provide greater or less contact with different portions of the implantable articles 100. In some examples, the polishing media 404 can use a combination of two or more different sizes of particles, such as porcelain or other non-rusting media, in conjunction with a solvent 302, such as methylene chloride. In various examples, at least a portion of the polishing media 404 includes particles having a size greater than 3 millimeters in diameter or across. In some examples, at least a portion of the polishing media 404 includes particles having a size less than about 1 millimeter in diameter or across. In an example, the polishing media 404 includes particles with respective sizes of about 1 millimeter in diameter or across, about 3 millimeter in diameter or across, and about 6 millimeters in diameter or across, such as in a respective 2:1:1 ratio. The larger particle sizes of the polishing media 404 can help generate enough inertia to polish the implantable articles 100, while the smaller particle sizes of the polishing media 404 can find their way into narrow interstices, such as to contact the smaller article portions 406 (e.g., corners formed by the intersection of two more angled article surfaces or portions).

The receptacle 304 can be filled with the polishing mixture 402 and implantable articles 100 to a level that allows movement of the particles of the polishing media 404 during agitation of the receptacle 304. In a tumble polishing example, the receptacle 304 can be sized so that a layer of polishing media 404 can slide down over the other polishing media 404 in the receptacle 304 during rotation of the receptacle 304, rather than being flung in the air to the gravitational bottom of the receptacle 304.

Figure 5:
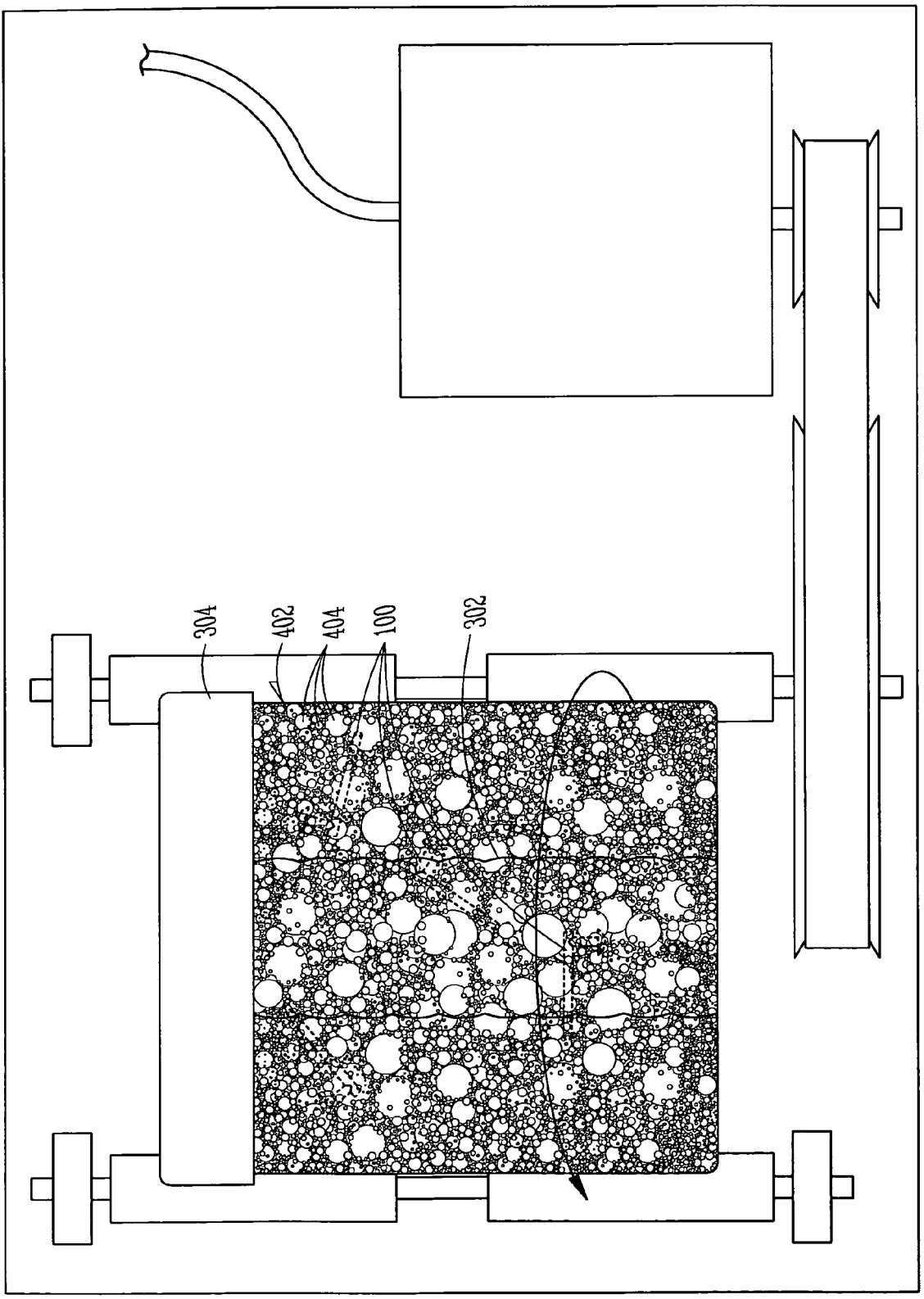
FIG. 5 illustrates an example of a schematic view of a tumbler device and a closed receptacle including a plurality of implantable articles, a swellable solvent, and polishing media.

FIG. 5 illustrates an example of a schematic view of a tumbler device 502 and a closed receptacle 304 enclosing a plurality of implantable articles 100 and a polishing mixture 402, including a swelling-promoting solvent 302, and polishing media 404. Once the solvent 302, polishing media 404 and implantable articles 100 to be polished are added to the receptacle 304, the receptacle 304 can be agitated for a time and at a speed sufficient to substantially remove any flash 104 (FIG. 1), sharp edges 102 (FIG. 1), uncured article material regions or any tool or machining marks from the surfaces of the articles 100.

Polishing can include tumble polishing in a rotating receptacle 304 mounted on a tumbler device 502, vibratory polishing in a vibrating bowl or other receptacle 304, or other method of agitation (e.g., shaking, stirring, or multiple directional mixing). A plurality of molded implantable articles 100 can be placed in the receptacle 304 along with the solvent 302 and the polishing media 404 and then tumbled, vibrated or otherwise agitated for a period of time at a speed sufficient to remove the surface irregularities without damaging the soft article material. The time period and polishing media 404 can be selected to achieve a desired degree of rounding, tapering or smoothing for the implantable articles 100. In certain examples, the polishing process can use a slow rotational tumbling that does not remove material from the articles 100 at a high rate. Therefore, the removal or polishing of flash 104 (FIG. 1) or sharp edges 102 (FIG. 1) can be easily monitored. In an example, the rotational tumbling of the receptacle 304 is performed for a time period of about 24 hours to about 72 hours. In some examples, the rotational tumbling or other method of agitation is performed for a time period of less than 24 hours, such as 1-6 hours. In certain examples, multiple directional mixing (e.g., via a figure-eight mixer) can be used to create rapid changes of direction, creating more force experienced by the implantable articles 100, thereby achieving a desired article surface finish in a timely manner.

After polishing, the implantable articles 100 can be separated from the polishing media 404 and the solvent 302, such as using a filtering process. After the implantable articles 100 are separated from the polishing media 404, any solvent 302 remaining on the articles 100 can be processed, encouraged or allowed to quickly evaporate, thereby allowing the articles 100 to return to their original size. In some examples, solvent evaporation from the implantable articles 100 can be expedited by placing the articles 100 in a warm oven (e.g., set at about 100° F.-200° F. or more) for a certain period of time (e.g., about 30 minutes). In some examples, solvent evaporation from the implantable articles 100 can be expedited by placing the articles 100 in a vacuum over. Optionally, the implantable articles 100 can be rinsed or otherwise cleaned with a cleaning solution (e.g., isopropanol) prior to use, such as in an ultrasonic cleaner. It is believed the present polishing process, at its completion, leaves the implantable articles 100 with relatively smooth surfaces, having minimal to no flash or uncured material regions, rounded edges, and a structure substantially free of residual solvents.

For quality control or other detection purposes, one or more polished implantable articles 100 can be tested for residuals solvent amounts using a headspace gas chromatographic method. For instance, residual methylene chloride and isopropanol of the implantable articles 100 can be quantitatively determined with a headspace gas chromatographic method using a flame ionization detector and a headspace autosampler. In some examples, two polished implantable articles 100 (e.g., lacrimal implants) can be extracted with about 1.0 milliliter of dimethylformamide or other organic solvent having a high boiling point at about 120° C. inside the headspace autosampler. The headspace can be injected into a gas chromatograph. The separation of the residuals solvents can be achieved with a fused silica capillary column coated with polyethylene glycol 20M stationary phase (USP G16), for example. The residuals solvents can then be detected by the flame ionization detector. In various examples, residual amounts of isopropanol and methylene chloride can be detected down to about 0.0469 micrograms and about 0.1125 micrograms, respectively. Implantable articles 100 having residuals of isopropanol and methylene chloride less than about 0.0469 micrograms and about 0.1125 micrograms, respectively, can be considered substantially free of residual solvents in some examples. The residual solvent amount(s) detected can be compared with established ICH Q3 guidelines.

EXPERIMENTAL EXAMPLE

Tumble Polishing of Lacrimal Implants

In order that the present polishing process can be more fully understood, the following example is given by way of illustration.

A 16-ounce glass tumbling receptacle was filled with approximately 200 milliliters of friction-imparting polishing media, including approximately 50% of 1 millimeter particle diameter porcelain burnishing media, 25% of 3 millimeter particle diameter porcelain burnishing media, and 25% of 6 millimeter particle diameter porcelain burnishing media. To this, 50 milliliters of methylene chloride solvent of a USP or NF grade and a plurality of implantable articles in the form of lacrimal implants were added. The receptacle and its contents were then placed on a tumbler device, which was switched on and set at a speed of about 50-60 revolutions per minute, and tumbled for about 35-72 hours.

After tumbling, the receptacle and its contents were poured out to separate the lacrimal implants from the polishing media. The lacrimal implants were then allowed to evaporate out remaining solvent and rinsed with a cleaning solution (e.g., deionized water). Sample lacrimal implants tumbled for 24 hours, 48 hours, and 72 hours were inspected under magnification and surface finish quality was observed. Each of the observed implants appeared to be highly polished with uniform removal rates.

Closing Notes:

Removing flash and otherwise improving the surface finish of silicone or other soft durometer implantable articles can be useful in situations that, for example, can benefit from a relatively high level of surface finish (e.g., medical implants), improved optical clarity, or rounded edges. It is believed that the present polishing process advantageously lends itself to use at various facilities producing silicone or other soft durometer implantable articles and further provides for low cost surface finishing of articles. It is further believed that the present polishing process can be valuable to achieving long-term comfort for patients implanted with polished articles such as lacrimal implants, for example.

The above Detailed Description includes references to the accompanying drawings, which form a part of the Detailed Description. The drawings show, by way of illustration, specific embodiments in which the invention can be practiced. These embodiments are also referred to herein as "examples." All patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method comprising:
    placing one or more lacrimal implants in a receptacle containing a polishing mixture, the polishing mixture comprising a swelling-promoting solvent to swell the one or more implants and a polishing media including particles having two or more different sizes, at least one of the particle sizes is about 6 millimeters across and a second particle size is less than about 6 millimeters across;
    causing the one or more lacrimal implants to be repeatedly impacted with the polishing mixture while in the swelled state so as to smooth one or both of a surface or an edge of the lacrimal implants; and
    separating the lacrimal implants from the polishing mixture, thereby producing one or more polished lacrimal implants.

2. The method of claim 1, further comprising swelling lacrimal implants using at least one of xylenes, naphthalene, toluene, or methylene chloride.

3. The method of claim 1, wherein repeatedly impacting the lacrimal implants includes tumbling the lacrimal implants and the polishing mixture together for a period of time and at a speed sufficient to smooth one or both of a surface or an edge of the lacrimal implants.

4. The method of claim 1, wherein repeatedly impacting the lacrimal implants includes at least one of removing article flash, removing uncured article material, rounding an article edge, or improving article optical clarity.

5. The method of claim 1, wherein separating the lacrimal implants includes removing residual solvent from the lacrimal implants.

6. The method of claim 5, further comprising detecting a residual solvent amount of the one or more polished lacrimal implants.

7. The method of claim 6, wherein detecting the residual solvent amount includes using a headspace gas chromatographic method using a flame ionization detector and a headspace autosampler to detect a residual of methylene chloride of about 0.1125 micrograms or greater.

8. The method of claim 1, wherein the second particle size is selected from the group comprising about 1 millimeter across, about 3 millimeters across, or less than about 1 mm across.

9. The method of claim 1, wherein at least one of the lacrimal implants comprise an implant body, including first and second portions, and extending from a proximal end of the first portion to a distal end of the second portion;
    the first portion defining a longitudinal proximal axis and the distal end defining a longitudinal distal axis;
    the implant body configured such that, when implanted in a lacrimal canaliculus, an angled intersection exists between the proximal axis and the distal axis for biasing at least a portion of the implant body against at least a portion of the lacrimal canaliculus located at or more distal to a canalicular curvature.

10. The method of claim 1, wherein the lacrimal implants comprise a silicone or polyurethane material.

11. The method of claim 1, further comprising cleaning the lacrimal implants, including contacting the implantable articles with a cleaning solution in a receptacle and agitating the receptacle for a period of time and at a speed sufficient to clean a surface of the lacrimal implants.

12. The method of claim 1, wherein the causing the implantable articles to be repeatedly impacted with the polishing mixture so as to smooth one or both of a surface or an edge of the lacrimal implants is for a time period of about 24 hours, about 48 hours or about 72 hours.

13. A method comprising:
    introducing into a receptacle contents comprising one or more silicone lacrimal implants and a polishing mixture, the polishing mixture including polishing media and a swelling-promoting solvent to swell the one or more implants, wherein the polishing media comprises a mixture of two or more different particle sizes, wherein at least one of the particle sizes in the polishing media is about 6 millimeters across and one of the particle sizes in the polishing media is less than 6 millimeters across; and
    agitating the contents of the receptacle for a time sufficient to remove one or more surface irregularities from the silicone lacrimal implants while the lacrimal implants are in a swelled state.

14. The method of claim 13, wherein agitating includes rotating the receptacle at a speed and for a time sufficient to substantially remove the one or more surface irregularities from the silicone lacrimal implants.

15. The method of claim 13, further comprising detecting one or more polished lacrimal implants substantially free of residual solvent using a flame ionization detector.

16. The method of claim 13, wherein the swelling-promoting solvent is xylenes, naphthalene, toluene, or methylene chloride.

17. The method of claim 13, wherein the agitating the contents of the receptacle for a time sufficient to remove one or more surface irregularities from the silicone lacrimal implants is for about 24 hours, about 48 hours or about 72 hours.

\* \* \* \* \*